United States Patent
Land et al.

(10) Patent No.: US 8,652,076 B2
(45) Date of Patent: Feb. 18, 2014

(54) ACTIVE HAND-EXTENSION/FLEXION DEVICE

(75) Inventors: Edward M. Land, Owings Mills, MD (US); H. Lee Mantelmacher, Owings Mills, MD (US); Rebecca German, Baltimore, MD (US); Marlis Gonzalez-Fernandez, Catonsville, MD (US); Gad Alon, Rockville, MD (US); John Staehlin, Westminster, MD (US); Ken Silver, Pikesville, MD (US); Wayne E. Moore, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/177,844

(22) Filed: Jul. 7, 2011

(65) Prior Publication Data

US 2012/0136284 A1    May 31, 2012

Related U.S. Application Data

(60) Provisional application No. 61/382,627, filed on Sep. 14, 2010.

(51) Int. Cl.
*A61H 1/00* (2006.01)

(52) U.S. Cl.
USPC ............ 601/40; 601/5; 601/33; 482/47

(58) Field of Classification Search
USPC ............ 601/5, 23, 24, 26, 33, 40, 84, 97, 98, 601/101; 2/161, 163, 159, 160; 482/47, 48, 482/49, 44, 45, 46, 124
See application file for complete search history.

(56) References Cited

U.S. PATENT DOCUMENTS

| | | | |
|---|---|---|---|
| 4,766,612 A | | 8/1988 | Patton, Sr. |
| 5,103,807 A | * | 4/1992 | Makaran ............ 601/40 |
| 5,453,064 A | | 9/1995 | Williams, Jr. |
| 7,601,130 B2 | | 10/2009 | Farrell et al. |
| 2006/0094989 A1 | | 5/2006 | Scott et al. |
| 2007/0123809 A1 | * | 5/2007 | Weiss et al. ............ 601/84 |
| 2009/0196463 A1 | | 8/2009 | Kuniz et al. |
| 2010/0030122 A1 | * | 2/2010 | Gaspard ............ 601/136 |
| 2012/0059290 A1 | * | 3/2012 | Yip ............ 601/40 |

OTHER PUBLICATIONS

Nathan, et al. "Design and validation of low-cost assistive glove for hand assessment and therapy during activity of daily living-focused robotic stroke therapy" Journal of Rehabilitation Research & Development. vol. 46, No. 5, pp. 587-602 (2009).
Northeastern University; ATLAS Bimanual Rehabilitation Glove; provides resistance in hand exercises http://www.northeastern.edu/news/stories/2009/12/capstoneglove.html.

* cited by examiner

*Primary Examiner* — Quang D Thanh
(74) *Attorney, Agent, or Firm* — Johns Hopkins Technology Transfer

(57) ABSTRACT

A hand movement device comprises a glove for positioning about a hand of a user, a first anchor element adapted to be positioned about a base surface of glove, a second anchor element adapted to be positioned at a tip of a finger portion of the glove, an active spring member positioned between the first and second anchor elements, said active spring member being fixedly secured to said first anchor element and moveable through said second anchor element to thereby allow said spring member to bend about a joint of the finger when said finger is flexed, an activating element positioned adjacent the active spring member to heat or cool said active spring member thereby causing the spring member to bend or straighten, and an intermediary support device for housing said spring element and for connecting the first anchor element to said second anchor element.

38 Claims, 7 Drawing Sheets

ACTIVE HAND-EXTENSION/FLEXION DEVICE

REFERENCE TO RELATED APPLICATIONS

This application claims the benefit of U.S. Provisional Patent Application No. 61/382,627, filed on Sep. 14, 2010, which is hereby incorporated by reference for all purposes as if fully set forth herein.

FIELD OF THE INVENTION

The present invention pertains to a movement device. More particularly, the present invention pertains to a movement device for hand extension and flexion.

BACKGROUND OF THE INVENTION

Millions of Americans (adults and children), including stroke victims and accidents due to traumatic brain injury (TBI) have lost the ability to open a partially paralyzed, clenched fist. Inability to open the hand precludes functional use of that hand and limits the functional use of the limb. Annually, in the US alone, a significant number of stroke survivors, estimated to be over a million, retain their ability to grasp with a varying degree of grip strength due in part to disuse brought about by the stroke. These individuals lack the ability to re-open their affected hand volitionally in order to release or accommodate objects. Many of these individuals, due to the nature of how a stroke affects the limbs, still are able to effectively control the shoulder and elbow. Consequently, the isolated loss of adequate finger motion imparts significant disability to stroke victims who otherwise should be able to functionally use their impaired upper extremity.

Most products currently available are bulky and difficult to use. Similarly, many devices are designed as therapeutic aides to permit exercising the fingers with the goal of recovery from an injury or act as a splint. In some cases, these devices measure the forces and motions of each finger providing valuable therapeutic information. These devices, in general, are not intended to assist the user in opening or closing the hand for the purpose of regaining utility of the limb.

Existing assistive devices use intrusive metal cables or employ awkward, oversized, exoskeleton housings for each finger and in some cases use small but heavy motors. Most of these devices have been designed to provide passive stretching of the fingers over a long period of time, although some, despite their bulky size, can be used to facilitate functional use of the hand in individuals who retain some grasp ability but lack hand-extension. In one such design, the suspension cable (suspension bridge-like) passive-opening device can only be worn at night to stretch the ligaments and must be worn in a fixed position to permit the fingers to stretch. Many prior art designs employ complex mechanical structures that are both difficult to manufacture, use, clean, or adjust, and are failure prone. Considering that no two hands are alike, rigid mechanical structures employing tensioning cables and supporting scaffolds are difficult, if not painful, to adjust and readjust to fit the hand.

Accordingly, there is a need in the art for a simple, convenient, mechanically robust movement device to allow opening and/or closing the fingers of hands of stroke victims and others who have lost all or part of the ability to move their fingers.

SUMMARY

According to a first aspect of the present invention, a movement device comprises a first anchor element adapted to be positioned adjacent a wrist of the user, a second anchor element adapted to be positioned at a tip of a finger of a user, an active spring member positioned between the first and second anchor elements, said active spring member being fixedly secured to said second anchor element and moveable through said first anchor element to thereby allow said spring member to bend about a joint of the finger when said finger is flexed, an activating element or remotely located source of heat positioned adjacent to or supplied to the spring member to heat or cool said active SMA spring member thereby causing the spring member to bend or straighten; and an intermediary support device disposed between said first anchor element and said second anchor element so as to prevent the active spring member from contacting joints of the user.

According to a second aspect of the present invention, a hand movement device comprises a glove for positioning about a hand of a user, a first anchor element adapted to be positioned about a base surface of glove, a second anchor element adapted to be positioned at a tip of a finger portion of the glove, an active spring member positioned between the first and second anchor elements, said active spring member being fixedly secured to said first anchor element and moveable through said second anchor element to thereby allow said spring member to bend about a joint of the finger when said finger is flexed, an activating element or remotely located source of heat positioned adjacent to or supplied to the spring member to heat or cool said active SMA spring member thereby causing the spring member to bend or straighten; and an intermediary support device for housing said spring element and for connecting the first anchor element to said second anchor element.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to an "active" device. The term "active" refers to embodiments using materials such as super memory alloys (SMAs), electroactive polymers (EAPs) or other materials that can be activated by heat, electricity, or other means to change shape or mechanical properties and thereby apply the required forces. The term "passive" applies to embodiments that rely on the elastic properties of bent or stretched materials to apply forces that are not activated by heat, electricity or other means to change the shape or mechanical properties of the material. However, combinations of active and passive materials can be used when beneficial to the needs of the user.

Figure 1A:
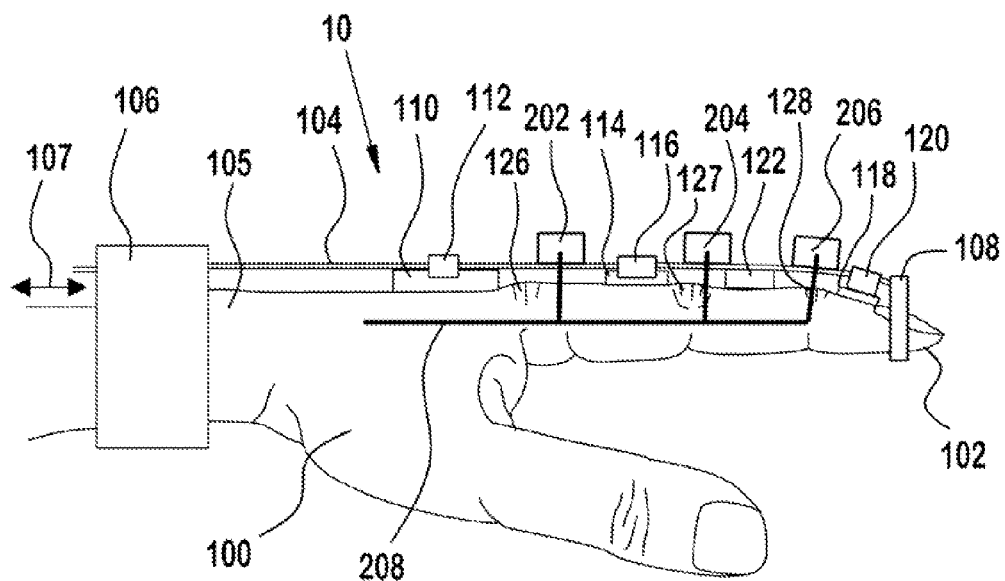
FIG. 1A illustrates a perspective view of an exemplary product according to the features of the present invention with the fingers in an extended or straightened position.
Figure 1B:
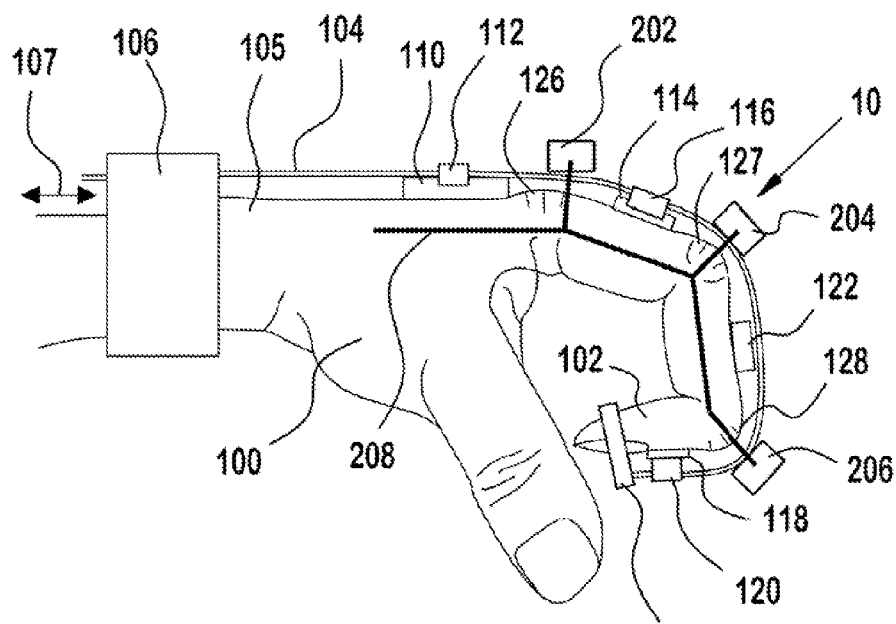
FIG. 1B illustrates a plan view of an exemplary product according to the features of the present invention with the fingers in a flexed position.
Figure 2:
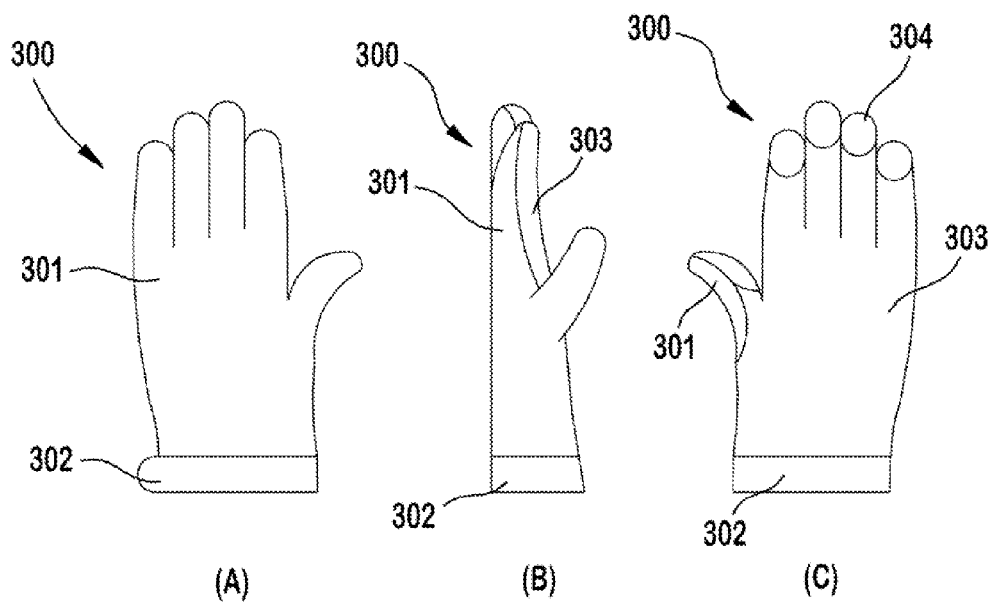
FIG. 2A illustrates a rear elevated view of an exemplary product according to the features of the present invention.
FIG. 2B illustrates a side elevated view of an exemplary product according to the features of the present invention.
FIG. 2C illustrates a front elevated view of an exemplary product according to the features of the present invention.
Figure 3:
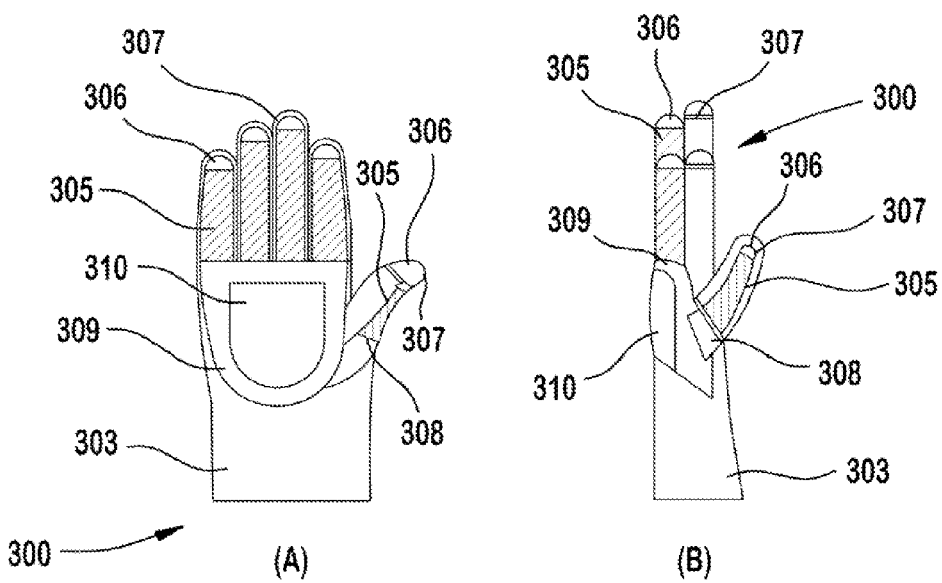
FIG. 3A illustrates a rear elevated view of the exemplary product with the glove shell removed according to features of the present invention.
FIG. 3B illustrates a side elevated view of the exemplary product with the glove shell according to features of the present invention.
Figure 4:
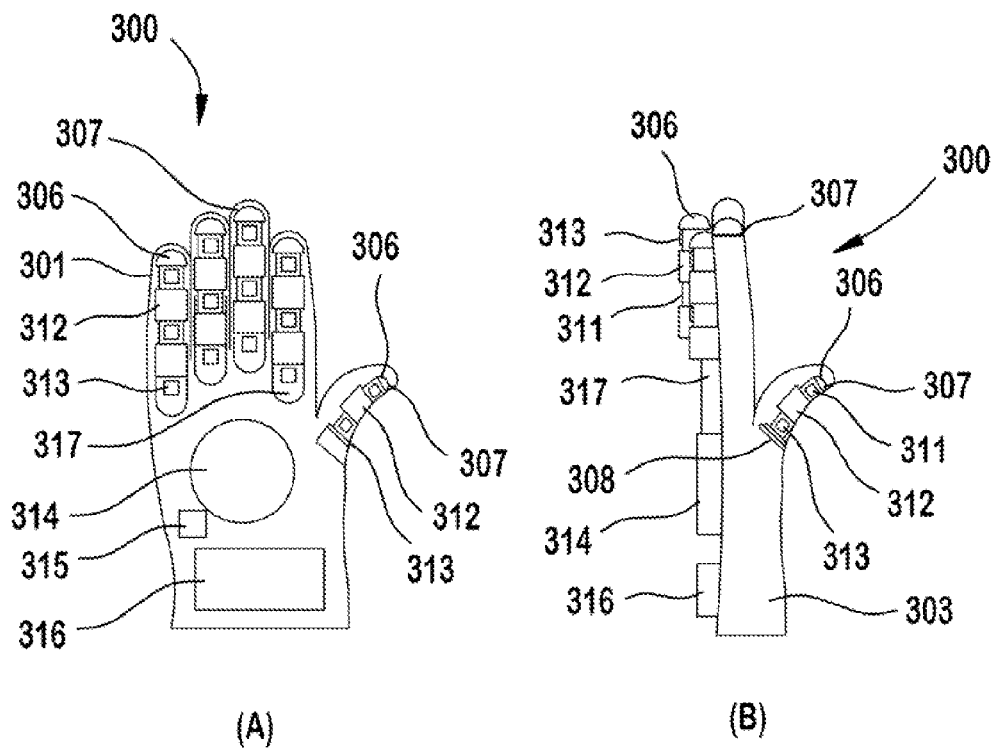
FIG. 4A illustrates a rear elevated view of the exemplary embodiment having the corrugated tubing removed according to features of the present invention.
FIG. 4B illustrates a side elevated view of the exemplary embodiment having the corrugated tubing removed according to features of the present invention.

With reference to FIGS. 1A and 1B, an exemplary embodiment of the movement device is illustrated. While the exemplary movement device 10 is shown in connection with a hand 100, it should be understood that the movement device 10 of the present invention can be used with any joint, including but not limited to, the wrist, elbow, knee, feet, and toes. In addition, while only one finger 102 is illustrated in the FIGS. 1A and 1B, it should be understood that features of the movement device may extend to one, some, or all fingers and/or thumb, depending upon application. That is, each and any number of fingers and thumb may be used in the movement device, which pertains equally to either the right or left hand, depending upon the needs of the user.

With reference in particular to FIG. 1A, the movement device 10 of the present invention includes an active spring member 104 adapted to bend about a joint of the appendage when the appendage is flexed—in this case, the finger points of the user. Preferably, the active spring member 104 is parallel or is appropriately disposed with respect to each appendage so that they can only bend in a single plane, and in some embodiments when used with a hand and at certain locations, corresponding to the desired movement at each interphalangeal and metacarpophalangeal finger joint (knuckle). A first anchor element 106 is adapted to be positioned adjacent a jointed appendage of a user at a first position. Preferably, the active spring member 104 is movable though the first anchor element 106 so that it may travel and be elongated without resistive force when the finger is bent. Anyone skilled in engineering can readily design many anchoring schemes that will permit a free length of the spring material 104 to slide as needed when the finger is bent to the position show in FIG. 1B.

As shown in FIGS. 1A and 1B, the first anchor element 106 is positioned beyond the wrist 105 so that the bending torsion of the active spring member 104 might, if needed, be used to assist in straightening the wrist. Alternatively, the first anchor element 106 may stop just short of the wrist, adjacent to outside of the hand. The first anchor element 106 may be affixed to the hand and/or wrist by several strips of, VELCRO® strap, or the like. In addition, the first anchor element 106 may be built into the structure of a glove, or glove-like appliance.

The active spring member 104 is positioned between the first anchor element 106 and a second anchor element 108. Preferably, the active spring member 104 is fixedly secured to the second anchor element 108 and moveable through the first anchor element 106 to thereby allow the active spring element 104 to bend about a joint of the finger when the finger is flexed. In the exemplary embodiment, the second anchor element 108 is placed at the tip of the finger. Preferably, the active spring member 104 is fixedly secured to the second anchor element 108 to statically constrain the end of the spring member 104 to the tip of the finger. However, importantly, the active spring member 104 should be unrestrained at the joint. The active spring element 104 is made from a shape memory alloy such as Nitinol (NiTi) or other SMA material. The active spring member 104 may include a flat bade, but may also include more than one flat blade disposed on top of each other.

An intermediary support device is disposed between the first anchor element 106 and the second anchor element 108 so as to prevent the active spring member 104 from contacting the joint(s) of the user. In the exemplary embodiment, the intermediary support device includes a series of pads 110, 114, and 118 disposed along the length of the finger 102. The pads 110, 114, and 118 may be held by means of a glove, strap, or the like. Associated with each pad 110, 114, and 118 are bushings 112, 116, and 120. The bushings 112, 116, and 120 provide low friction guidance of the spring member 104 as is slides forward and backwards through the first anchor element 106, as the finger is bent and straightened. Preferably, the pads are disposed between the joints 126, 127, and 128. However, the number and location of pads can vary, depending upon application and design preference. Likewise, additional pads, such as pad 122, may be provided without a bushing, depending upon application and design preference. Accordingly, the intermediary support device provides support along non-joint positions of the appendage so that the spring member 104 is unable to apply any significant forces to the joints of the appendage. As such, the bushings 112, 116, and 120 should be built in a manner to straighten and elevate the spring member 104 to prevent contact with the fingers.

With continued reference to FIGS. 1A and 1B, one or more activating elements 202, 204, and 206 may be positioned adjacent the active spring member 104 to heat or cool the active spring member 104 thereby causing the spring member to bend or straighten. The activating member may be a Peltier thermoelectric heating/cooling device, also known as a thermoelectric cooler (TEC) or a thermoelectric device (TED). TECs function to allow one surface of the device to be made hotter while the other side is made cooler by the application of a small direct electrical current. By reversing the current, the opposite surfaces become colder or hotter which increases the speed of the transformation and eliminates the need for external cooling or heating.

The TECs 202, 204, 206 may be affixed to the spring element 104 using thermally conductive flexible adhesives or other means. The application of heat or cold to the SMA need not be in the exact location of bending action because the SMA material conducts heat well. For this reason the location of the SMA material as it bends (flexes or extends) above the joints can be imprecise. The SMA material deforms in the location conditioned for memory action without regard to the exact location of the source of cooling or heating provided by the TEC device. Similarly, the TEC units may be placed within the structure of a glove, glove-like appliance or remotely, on the arm or clipped to the patient's belt in a manner to position the TEC appropriately. The SMA alloy should be preselected such that a temperature difference of 20 degrees, more or less, can cause the SMA material to revert to its preconditioned (annealed), curved (hand-flexion) or straight (hand-extension) form shown in FIG. 1A or 1B. One having ordinary skill in the art would understand that the use of more or fewer TECs and/or associated bushings, pads, straps or related fixtures and structures to accomplish different combinations of flexion and extension, including the wrist 105, are envisioned within the scope of the present invention.

According to an exemplary design, at temperatures above about 20° C., the SMA may take the curved form shown in FIG. 1B. Thus, in most comfortable room temperature environments the device will reside in the curved configuration of FIG. 1B. Then by cooling the surface of the material that contacts the SMA at each of the locations shown 202, 204, 206 (for example, to 10° C.), the material will revert to its straight shape with substantial force thus opening the finger to the position shown in FIG. 1A. The application of such small temperature differences causes no discomfort to the user or excessive battery consumption. If the current to the TECs is turned off and the device is allowed to heat up, or if the current is reversed thus deliberately heating the SMA, the actuator 200 will return to the curved shape of FIG. 1B. This embodiment therefore is usable to close the fingers of a user who cannot do so, or using a separate, annealed "straight" blade(s) open the fingers, depending on the need. Of course a single (or multiple) SMA can also be conditioned to reside in the straight position of FIG. 1A and another corresponding SMA conditioned to transition to the curved shape upon a temperature change (from hot to cold or from cold to hot), depending upon application and design preference. It is important to note that all temperature extremes are to be considered "comfortable" to the patient.

Wiring is required to supply current to the TECs and is indicated schematically in FIGS. 1A and 1B as 208. The arrow 210 indicates that the wire bundle returns to a control unit of arbitrary design located elsewhere and not shown. As one familiar the fundamentals of electricity will readily appreciate, two wires are required as a minimum if all TECs are wired in parallel, whereas each TEC could have a separate pair of wires and be controlled individually if needed. The present invention uses a commonly available SMA such as Nitinol in shapes discussed above, flat ribbons, rods, stacks of flat ribbons or combinations thereof to provide electrical control of bending forces (via temperature regulation), rather than tensile forces.

In FIGS. 1A and 1B, the application of heat or cold has been discussed in terms of using Peltier TEC devices. Alternatively, other types of heating devices can be used. For example, intimate-contact, resistive heaters may be designed and formed to the specific needs of the user. Given that these devices can only supply heat and cannot affect cooling like a TEC, cooling may be accomplished in other ways, as will be described in more detail below. In addition, one having ordinary skill in the art would appreciate that there are many ways to heat or cool an SMA, including TECs, resistive heaters, fluid flow, and even air flow though tubing.

The thickness, width and number of the SMA strips or rods are used to determine the bending force applied at a particular joint. Sections of SMA material between the joint can be configured in a variety of ways. The active spring member can have other materials affixed to its surface to provide stiffness (and/or resistance) between the finger sections or at the joints if this should prove useful or necessary for a particular patient. The SMA material can also be located on the inside of the hand, running under the finger instead of on top using bending forces instead of tension forces to accomplish motion.

The assembly of components shown in FIGS. 1A and 1B schematically represents a novel embodiment of SMA material used in a bending mode rather than elongation and contraction, such application of SMA being unique in addressing the problem of finger manipulation. One skilled in design can readily appreciate, without further elaboration of detail, that the components illustrated can be built into a glove or similar easy-to-wear, low-profile, and esthetically pleasing device. Similarly a wide variety of fixtures can be made to permit the device to be worn without the fabric of a glove, one such concept being a simple arrangement of rings through which the fingers can slide and onto which are affixed the components of the invention shown.

With reference to FIGS. 2-11, another exemplary embodiment of the hand movement device 300. With reference to FIGS. 2(A)-(C), the hand movement device 300 includes a glove shell 301 for securing the mechanisms of the hand movement device 300. The glove shell 301 preferably has an adjustable wrist strap 302 for adjusting to a wrist of a user. The glove shell 301 includes a base portion 303 of the glove shell 301. Preferably, the tips of the gloves including tactile fingertip panel windows 304. Preferably, the panel windows 304 are made from very thin, minimally, stretch resistant fabric such as: Type I, ripstop, Nylon parachute cloth, Kevlar, Nomex, silk, or reinforced cotton which allows the material to conform to the finger tip and provide the user with some tactile feel during use.

With reference to FIGS. 3A and 3B, the hand movement device includes an intermediary support 305 for connecting the first anchor element to said second anchor element 309. Preferably, the intermediary support device 305 includes a corrugated tube for housing one or more active spring members 318 (see FIG. 5), e.g., actuator blades annealed in curves for hand closing and active spring member 311, e.g., actuator blades for hand opening, and one or more activating elements 313. The intermediary support device 305 may also house a number of bushings 312 that are used along the spring element to stabilize and support it along the finger and between the joints.

Use of the corrugated tube allows for the second anchor element 306 to be screwed into a first end of the corrugated tube. The second anchor elements 306 may then be secured to the tip of the glove 303 by a lifting strap 307 or the like. Preferably, the second anchor element 306 includes a hook for securing to the lifting strap. However, it should be understood that the second anchor element may be secured to the tip of the finger portion of the glove in many other ways, according to design preference and application.

The other end of the corrugated tube is secured to the first anchor element 309. In an exemplary embodiment, the first anchor element 309 is a housing manifold. Each of the corrugated tubes may be secured to the housing manifold by screwing into holes 350 of the housing manifold 309 (See FIG. 6). The housing manifold 309 contains and protects the control units (as will be described in more detail below), while also providing a channel to provide heating/cooling air to the intermediary support device 350 (corrugated tubing). Preferably, the housing manifold 309 includes an access door 310, which permits assembly and storage of components, as shown in FIGS. 3A and 3B. The housing manifold may be attached to the glove shell 301 by way of snaps, or the like.

Like the intermediary support device 305 for the fingers, the intermediary support device 305 for the thumb includes a second anchor element 306 which is secured to a lifting strap 307 on the glove, as shown in FIGS. 3A and 3B. However, another end of the intermediary support device 305 is secured to a thumb articulation joint 308, which holds the proximal end of the thumb blade while allowing for rotation as well as flexion and extension of the thumb.

Figure 12:
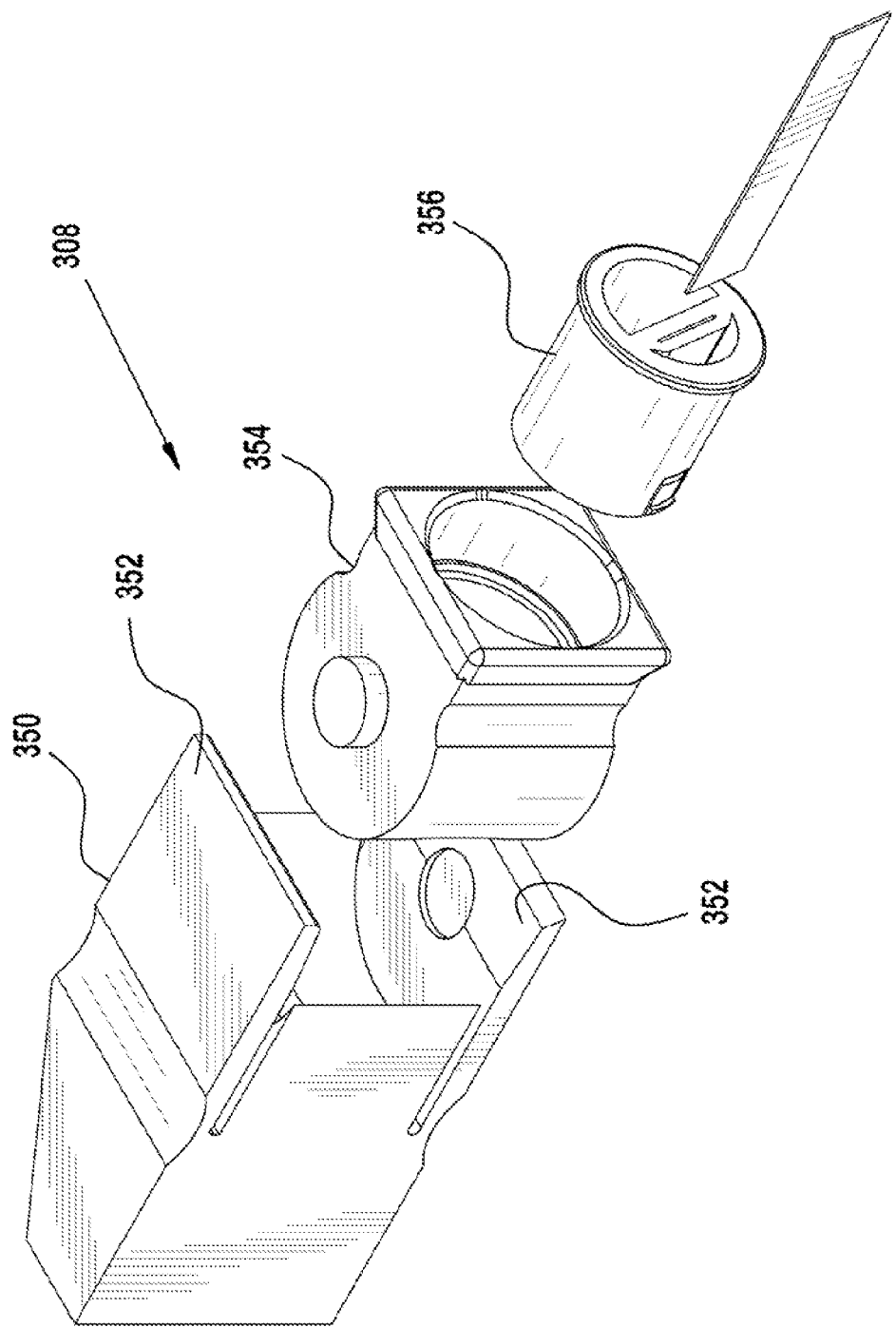
FIG. 12 is an exploded perspective view of the thumb articulation means according to features of the present invention.

With reference to FIG. 12, the thumb articulation joint 308 includes a support element 350 including twin downward facing cantilever support members 352 which protrude below the housing with incoming chamfered slides on each support member 352 (complementing the placement of the user's thumb). An armature bushing support housing 354 is equipped with robust, pivot supports to be mated and demated with the housing manifold for ease of assembly and to effect repairs. Additionally, the armature provides egress for the electrical system components and pivots with the thumb to sweep in palmar abduction. Finally, a bushing sleeve 356 provides actuator blade anchorage, mirror rotation and an air passage for internal cooling if and where needed. The bushing 356 is designed to lock into place and is easily removed when needed.

Figure 5:
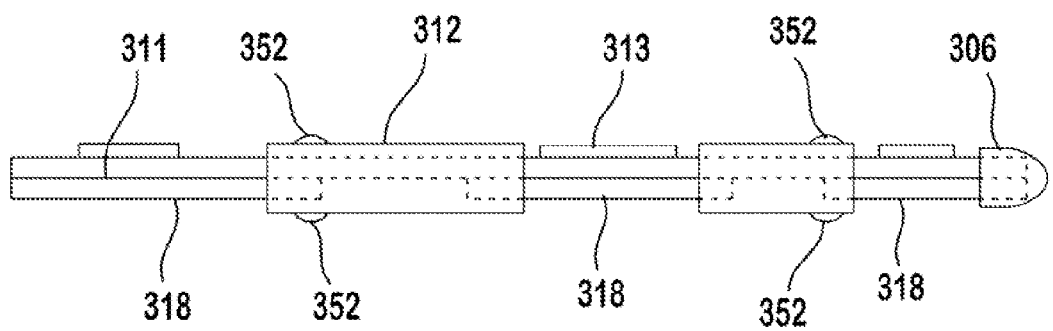
FIG. 5 illustrates a side view of an exemplary embodiment of the active spring member according to features of the present invention.
Figure 6:
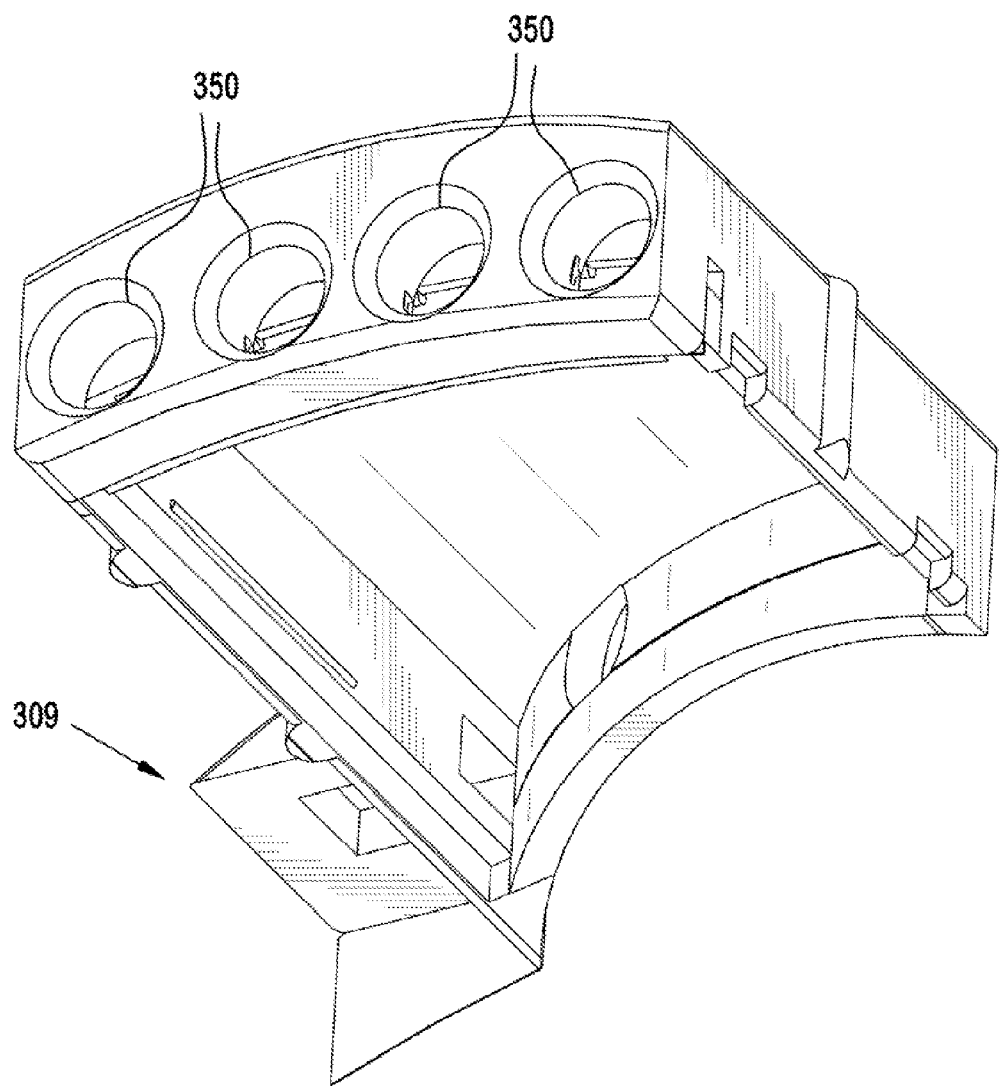
FIG. 6 illustrates a perspective view of an exemplary housing according to the features of the present invention.
Figure 7:
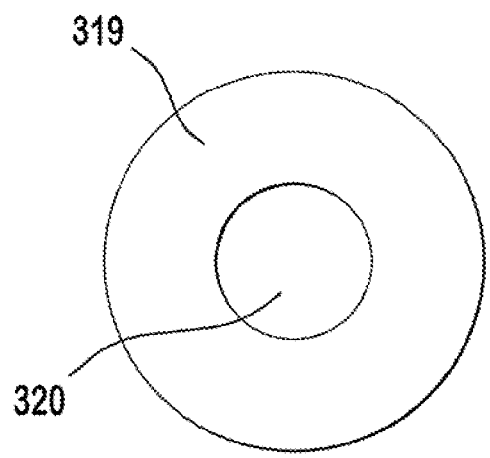
FIG. 7 illustrates an EMG array according to features of the present invention.
Figure 8:
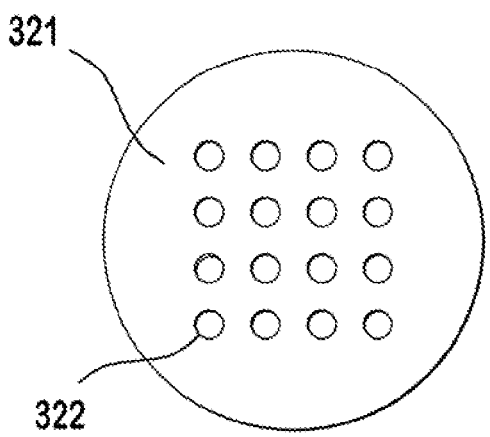
FIG. 8 illustrates an EMG channel pickup according to features of the present invention.

With reference to FIGS. 4A, 4B, and 5, internal components of the hand movement device 300 are illustrated (with the corrugated tubing and housing manifold removed). As described above, one or more active spring members 318 (FIG. 5) are provided. In addition, bushings 312 are provided along the spring element to stabilize it along the finger, and to hold the active spring member straight over phalangeal regions of the fingers. The bushings 312 may include threaded features 352 to allow the bushings to screw into the tubing. However, it should be understood that any numbers of blades may be used, and annealed according to design preference and application.

As described above, the second anchor element 306 includes a hook for securing to a lifting strap 307, while the lower end of the blades are held down by retention rods 317, which allow the blades 311 to splay. The metal retention rods are latched into place in the forward area of the housing manifold in a manner that restricts vertical travel but allows for swinging motion needed to splay the fingers.

Figure 9:
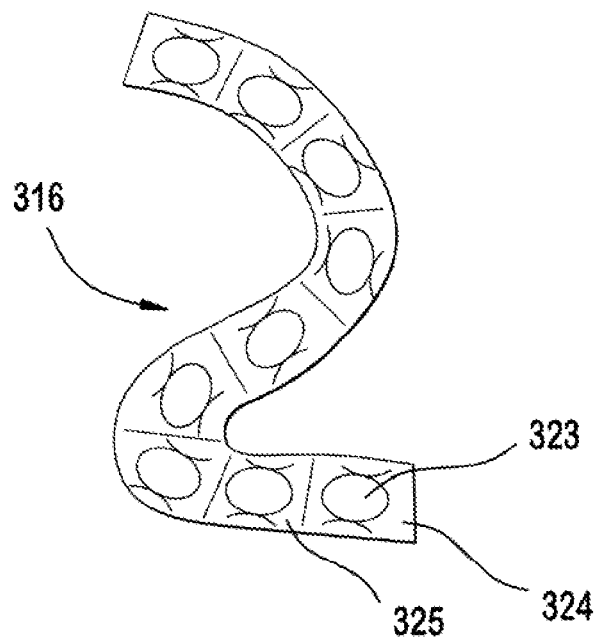
FIG. 9 illustrates a battery pack to be used in connection with a microprocessor according to features of the present invention.
Figure 10:
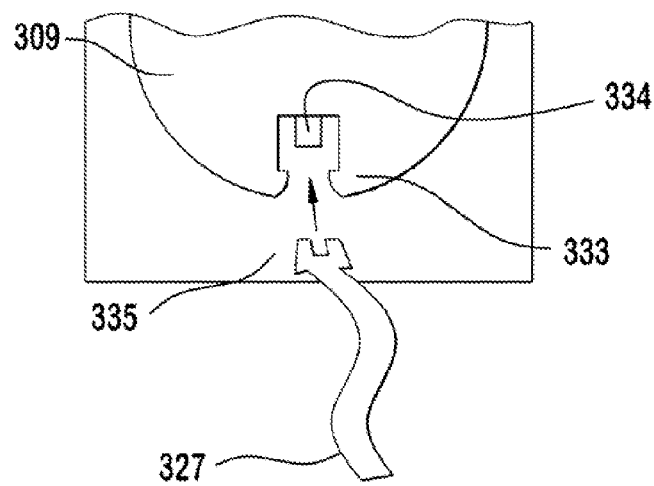
FIG. 10 illustrates connection of tubing to the manifold for cooling the activating element according to features of the present invention.
Figure 11:
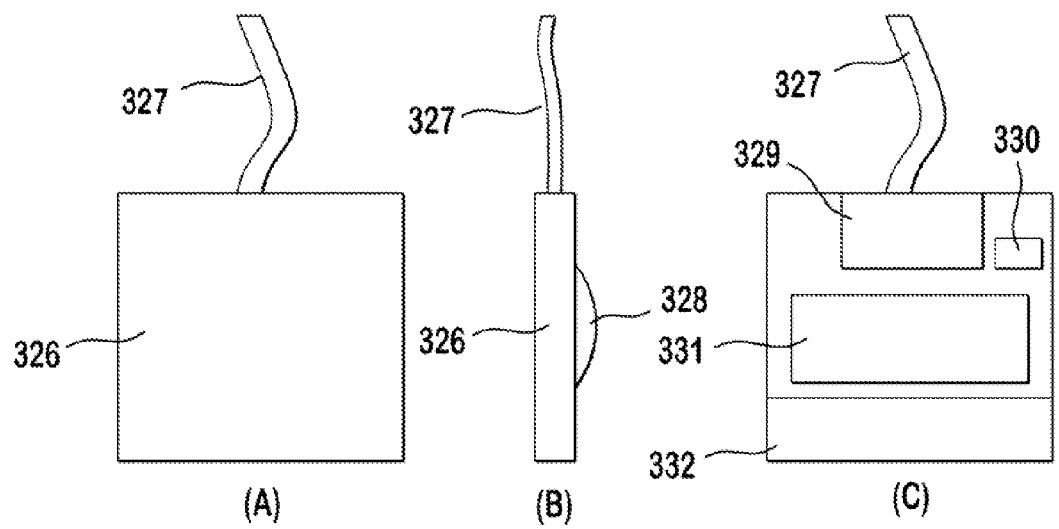
FIG. 11A illustrates a rear elevated view of an external supply pack for activating the movement device according to features of the present invention.
FIG. 11B illustrates a side elevated view of the external supply pack for activating the movement device according to features of the present invention.
FIG. 11C illustrates a front elevated view of the external supply pack for activating the movement device according to features of the present invention.

According to an exemplary embodiment, the hand movement device 300 may include a microprocessor, such as a cell phone microprocessor or the like, a receiver 315 and a (cell phone type battery unit or battery pack 316, as shown in FIGS. 4A and 4B. With reference to FIG. 9, the battery pack 316 includes a series of button batteries 323 that are daisy chained through a number of CE approved, connections 324, and include battery leads 325 which allow the batteries 323 to be pushed through to the next connection.

If using the device wirelessly, a remote transmitter may send the necessary signals to activate the hand movement device. For example, With reference to FIGS. 7 and 8, an EMG array 319 having a receiver/transmitter 320 may be used. In particular, the EMG may include a 16-channel EMG 321 with 16 individual pickups 322. As is known in the art, an EMG can be placed at a position on the body with active working muscles. Amplitudes of the EMG signals obtained from the active working muscles function to operate the hand movement device 300.

The EMG signals are sent to the receiver 315, and are processed in the microprocessor 314. The microprocessor includes externally, programmable software that allows the activating elements 313 to be electrically activated, to thereby heat or cool the device. However, activating element may also be operated by directing cooling/heating air through the tubes and remotely locating a conditioned fluid source via tubing to affect finger actuation.

With reference to FIGS. 10 and 11A-C, an external supply pack with fan or pump 326 may be provided to direct a heating or cooling supply to the housing manifold 309 (FIG. 10) by way of tubing 327 or the like. Preferably, housing manifold 309 includes a recessed nipple 334, which provides an interface between the tubing 327 and the manifold 309. The tube 327 is secured in a shielded nozzle port 333 of the housing manifold 309, and retained there by a barbed interface 335.

With reference to FIG. 11C, the tubing 327 is connected to a fluid heater/cooler 329, which provides a hot or cold flow through the tubing 327, and is directed to the intermediary support device 305. The external supply pack 326 may also include it own microprocessor 331, battery pack 332, fan or pump and receiver/transmitter 330, so that the hand movement device 300 may be controlled remotely. The external supply pack 326 may also include a belt hook 328, which allows the external supply pack 326 to be secured to the user.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:
1. A movement device, comprising:
a first anchor element adapted to be positioned adjacent a wrist of the user;
a second anchor element adapted to be positioned at a tip of a finger of a user;
an active spring member having a proximal end and a distal end, said active spring member extending between the first and second anchor elements, said distal end of the active spring member being fixedly secured to said second anchor element and moveable through the proximal end of the active spring member secured to said first anchor element to thereby allow said spring member to bend about a joint of the finger when said finger is flexed;

an activating element or remotely located source of heat positioned adjacent to or supplied to the active spring member to heat or cool said active spring member thereby causing the active spring member to bend or straighten; and an intermediary support device disposed between said first anchor element and said second anchor element so as to prevent the active SMA spring member from contacting joints of the user.

2. The movement device of claim 1, wherein the intermediary support device includes a series of pads which cushion and elevate the active spring member above a knuckle area.

3. The movement device of claim 2, further including a bushing associated with each pad such that each said bushing provides low friction guidance of the active spring member as it slides through said first anchor element.

4. The movement device of claim 1, wherein the active spring member is a flat blade.

5. The movement device of claim 4, wherein the active spring member includes more than one flat blade disposed on top of each other.

6. The movement device of claim 1, wherein said active spring member is made from a shape memory alloy.

7. The movement device of claim 6, wherein the shape memory alloy is Nitinol (NiTi) or other SMA material.

8. The movement device of claim 1, wherein the active spring member is unrestrained at the joint.

9. The movement device of claim 1, wherein said active spring member includes a series of spring members disposed parallel across tops of the fingers.

10. The movement device of claim 1, wherein the activating member is a thermoelectric cooling/heating device.

11. The movement device of claim 10, wherein the thermoelectric cooling/heating device is activated by an electric circuit.

12. A hand movement device, comprising:
a glove for positioning about a hand of a user;
a first anchor element adapted to be positioned about a base surface of glove;
a second anchor element adapted to be positioned at a tip of a finger portion of the glove;
an active spring member having a proximal end and a distal end, said active spring member extending between the first and second anchor elements, said proximal end of the active spring member being fixedly secured to said first anchor element and moveable through the distal end of said active spring member secured to said second anchor element to thereby allow said spring member to bend about a joint of the finger when said finger is flexed;
an activating element or remotely located source of heat positioned adjacent to or supplied to the spring member to heat or cool said active spring member thereby causing the spring member to bend or straighten; and
an intermediary support device for housing said spring element and for connecting the first anchor element to said second anchor element.

13. The hand movement device of claim 12, wherein the intermediary support device includes a corrugated tube for housing the active spring member and activating element.

14. The hand movement device of claim 13, wherein the second anchor element is screwed into a first end of the corrugated tube.

15. The hand movement device of claim 14, wherein a second end of the corrugated tube is screwed into the first anchor element.

16. The hand movement device of claim 13, wherein the first anchor element is a housing manifold having a plurality of openings for receiving and securing each one of the corrugated tube.

17. The hand movement device of claim 16, wherein housing manifold includes an access door for permitting assembly and storage of components.

18. The hand movement device of claim 12, wherein the second anchor element includes a hook for attaching to a lift strap secured on above a tip of the finger.

19. The hand movement device of claim 12, wherein the active spring member is made from a shape memory alloy.

20. The hand movement device of claim 19, wherein the shape memory alloy is Nitinol (NiTi) or other SMA material.

21. The hand movement device of claim 12, wherein the active spring member includes a flat blade.

22. The hand movement device of claim 21, wherein the active spring member includes more than one flat blade disposed on top of each other.

23. The hand movement device of claim 12, wherein the active spring member is unrestrained at the joint.

24. The hand movement device of claim 12, further including a series of spring members disposed parallel and side by side across tops of finger portions of the glove.

25. The hand movement device of claim 12, further including a covering, said covering being removably securable to said glove.

26. The hand movement device of claim 13, further including support bushings for holding said active spring member straight over phalangeal regions of the finger, said support bushings including attachment elements which allow the support bushings to be screwed into the corrugated tube.

27. The hand movement device of claim 12, further including a thumb articulation joint for holding a proximal end of thumb blade and for allowing for rotation of the thumb.

28. The hand movement device of claim 12, further including tactile panel windows disposed at finger tip portions of the glove.

29. The hand movement device of claim 12, further including a microprocessor.

30. The hand movement device of claim 29, wherein the microprocessor includes a receiver/transmitter for the communication of control signals for operation of said activating element.

31. The hand movement device of claim 30, wherein said receiver is wireless.

32. The hand movement device of claim 29, further including a battery unit for operation of the microprocessor and activating element.

33. The hand movement device of claim 32, wherein the battery unit includes a cell phone battery or series of button batteries that are connected to each other and leads for allowing batteries to be pushed to a next connector and disposed of when sufficiently depleted.

34. The hand movement device of claim 22, further including retention rods for retaining ends of the more than one flat blade and for allowing the more than one flat blade to splay.

35. The hand movement device of claim 29, further including an EMG array for communicating signals with said microprocessor.

36. The hand movement device of claim 16, further including an external supply pack for supplying heating and cooling fluid to said activating element.

37. The hand movement device of claim 36, wherein said external supply pack is connected to said housing manifold via tubing.

38. The hand movement device of claim 36, further including a microprocessor disposed in the external supply pack for receiving control signals from an EMG transmitter.

\* \* \* \* \*